United States Patent [19]

Gould

[11] Patent Number: 4,995,141

[45] Date of Patent: Feb. 26, 1991

[54] METHOD AND APPARATUS FOR FACILITATING PRODUCT CHANGEOVER IN THE MANUFACTURE OF FLUFF PADS FOR DISPOSABLE DIAPERS

[75] Inventor: Steven G. Gould, Denmark, Wis.

[73] Assignee: Paper Converting Machine Company, Green Bay, Wis.

[21] Appl. No.: 552,766

[22] Filed: Jul. 16, 1990

[51] Int. Cl.⁵ ............... D01G 25/00; D04H 5/05
[52] U.S. Cl. .................... 19/148; 264/121; 425/80.1; 28/104
[58] Field of Search .............. 19/145.7, 148, 301, 19/304, 308, 0.56; 28/104, 105, 106; 604/358; 264/121, 364, 517; 425/80.1, 81.1

[56] References Cited

U.S. PATENT DOCUMENTS

| | | | |
|---|---|---|---|
| 2,425,004 | 9/1947 | Rabell | 604/358 |
| 3,599,293 | 8/1971 | Nystrand et al. | 19/145 X |
| 4,666,647 | 5/1987 | Enloe et al. | 19/308 X |
| 4,674,966 | 6/1987 | Johnson et al. | 19/148 X |

FOREIGN PATENT DOCUMENTS 1234464  5/1986  U.S.S.R. ............... 19/304

Primary Examiner—Werner H. Schroeder
Assistant Examiner—John J. Calvert
Attorney, Agent, or Firm—Tilton, Fallon, Lungmus & Chestnut

[57] ABSTRACT

A method and apparatus for facilitating product changeover in the manufacture of fluff pads for disposable diapers which employs a side shifting drum equipped with removable pad forms.

8 Claims, 3 Drawing Sheets

METHOD AND APPARATUS FOR FACILITATING PRODUCT CHANGEOVER IN THE MANUFACTURE OF FLUFF PADS FOR DISPOSABLE DIAPERS

BACKGROUND AND SUMMARY OF INVENTION:

This invention relates to a method and apparatus for facilitating product changeover in the manufacture of fluff pads for disposable diapers and, more particularly, to the operation and construction of a forming drum.

Drum forming for making fluff pads is well known—see, for example, co-owned U.S. Pat. No. 3,599,293. Typically, however, product changeover has represented a problem in that a significant amount of time was spent in removing the forming hood from over the drum and then laboriously unbolting each one of the pad forms. In addition, if the pad repeat length (distance between leading edge of each pad on the drum) is changed, the corresponding change in drum diameter necessitated replacement or readjustment of the seals on the forming hood to match the new diameter.

It is therefore an object of this invention to simplify the changeover process to reduce the burden on the machine operators and improve the production efficiency.

According to the invention, fluff from a delivery hood is drawn generally inwardly to a rotating drum having a plurality of circumferentially extending screen forms releasably mounted thereon and wherein the drum is shifted axially from under the hood and thereafter each of the screen forms is replaced sequentially with another plurality of different sized screen forms.

Other objects and details of the invention may be seen in the ensuing specification.

The invention is described in conjunction with the accompanying drawing, in which FIG. 1 is a side elevational view of apparatus for practicing the invention;

Figure 1:
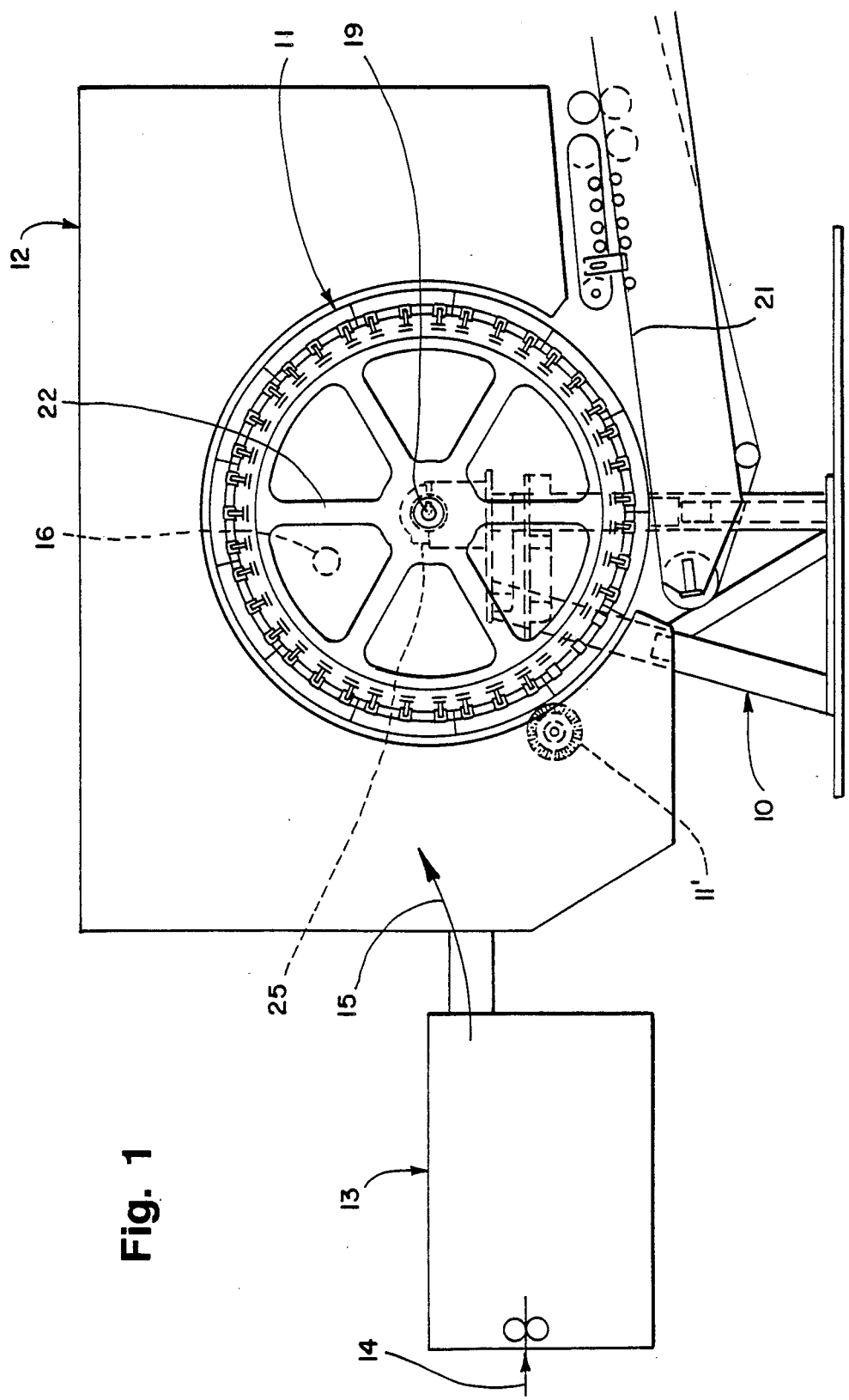

DETAILED DESCRIPTION:

In the illustration given and with reference first to FIG. 1, the numeral 10 designates generally a frame for supporting the forming drum generally designated 11 and the forming hood generally designated 12. Operationally associated with the frame 10 is a hammermill generally designated 13 which may be free-standing or incorporated as part of the frame 10. The hammermill 13 receives a continuous pulp web 14 and converts it to fluff which flows into the hood 12 as at 15. This is done under the influence of a vacuum conduit means—see the upper central portion of FIG. 2 where one such conduit is designated 16. In accordance with conventional practice, the conduit 16 is connected to a fan or compressor which exhausts air from the interior of the drum and thus causes the fluff to be deposited on the screen portions 17 of the forms 18—compare FIGS. 3–5.

OPERATION GENERALLY

A pulp web 14 (see the left hand portion of FIG. 1) is introduced into a hammermill where the web is ground into fluff particles exiting as an air stream 15 into a forming hood 12. The stream is developed by a vacuum applied as through the conduit 16 (see also FIG. 2) to direct the fluff particles radially inwardly to the drum 11. The fluff particles are stopped by screen portions 17—see FIGS. 3–5—on pad forms 18. The drum 11 has a plurality of circumferentially extending pad forms releasably mounted thereon as can be appreciated from a consideration of FIG. 4 where one of the forms has been removed.

Figures 2, 5:
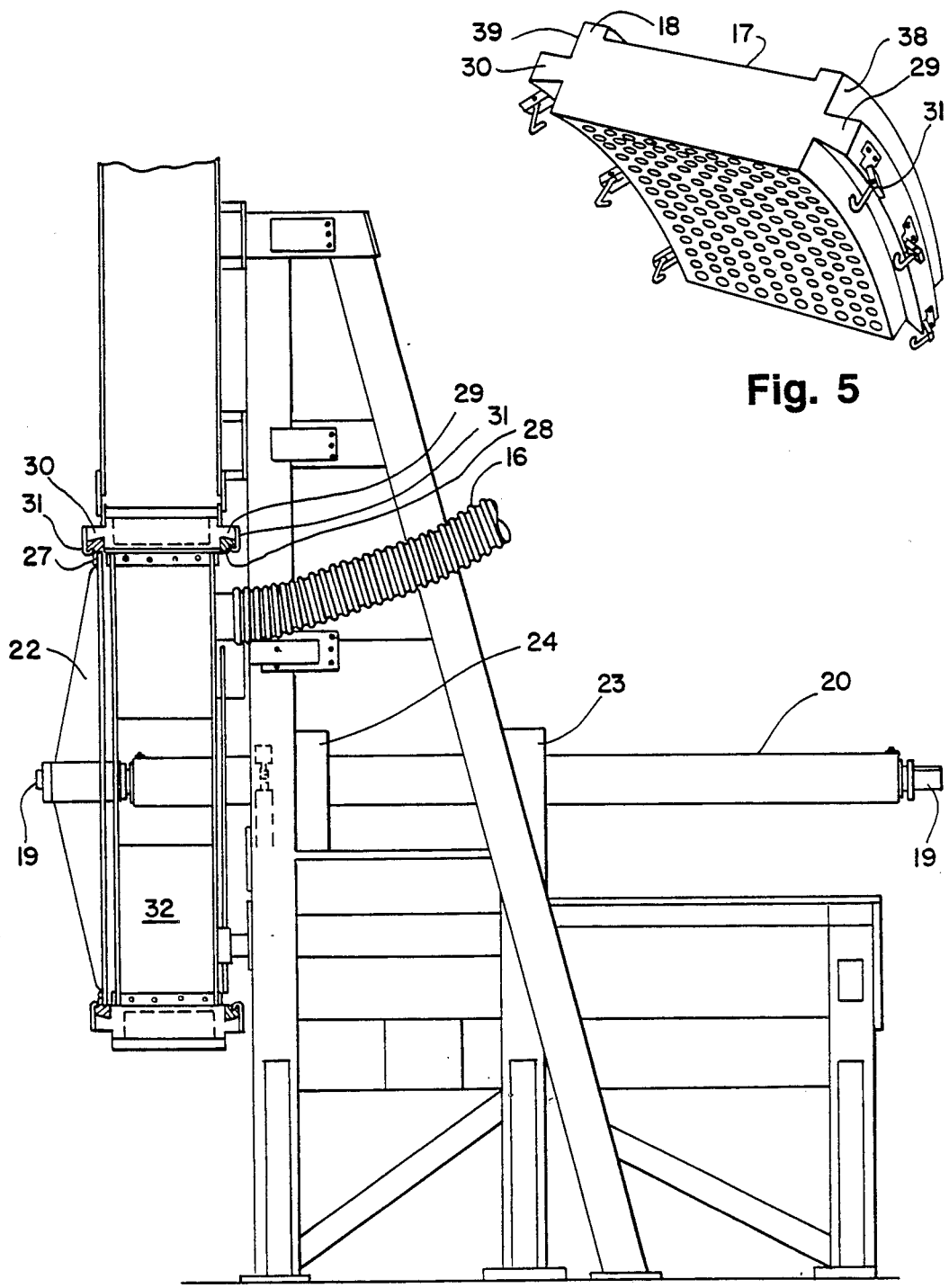
FIG. 2 is an end elevational view of the apparatus of FIG. 1.
FIG. 5 is a perspective view of a pad form.

The drum 11 is mounted on a shaft 19 which extends out of both ends of the translational support tube 20—see FIG. 2—and is rotated to build up a pad. A conventional scarfing wheel as at 11' (see FIG. 1) is mounted on the frame 10 within the forming hood 12 and ultimately the pads are picked up on an exit conveyor 21 to be sandwiched between a moisture impervious web (usually polyethylene) and a moisture pervious web (usually non-woven).

DRUM CONSTRUCTION

The drum construction (compare FIGS. 1, 2 and 4) includes a spider 22 which is fixed to the end of the shaft 19. From a consideration of FIGS. 2 and 3, it will be seen that the frame 10 is equipped with spaced bearings 23 and 24 and a fixed clamp 25 with the spider being mounted on the left hand protrusion of the shaft 19 from the translational support tube 20. The shaft 19 is rotated by a drive member such as a pulley gear 26 (see the right hand end of FIG. 3) which is mounted on the right hand protrusion of shaft 19. Thus, the shaft 19 is rotatably mounted in the translational support tube 120 which is releasably clamped in place by the clamp 25.

Figure 4:
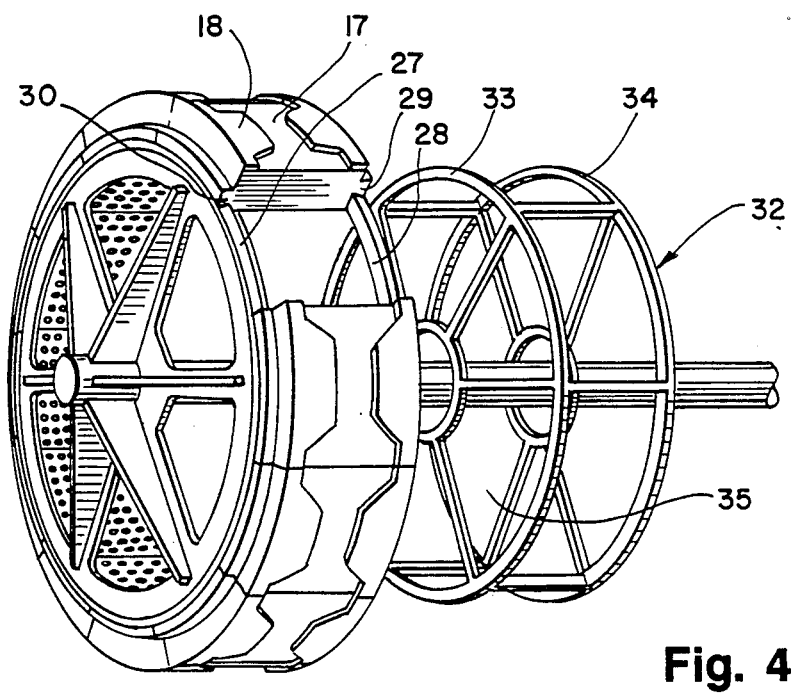
FIG. 4 is a fragmentary perspective view showing the forming drum in its position facilitating pad form changeover.

Fixed to the outer ends of the spider 22 is a ring 27 (compare FIGS. 2 and 4). Inboard of the ring 27 is a second ring 28 which is only connected to the ring 27—and this through the pad forms 18. It will be seen that the pad forms 18 (see particularly FIG. 5) have a generally arcuate shape and are equipped along opposite sides with arcuate flanges 29 and 30 which fit over the rings 28, 27 respectively. The flanges 29, 30 are equipped with over-center latches 31 which clamp the pad forms to each ring and thus develop a rigid, unitary construction.

Fitted with the drum 11—more particularly, the axially spaced rings 27, 28 is a stationary plenum 32 (see FIG. 2). This is mounted on the frame and is sealingly related to the drum rings 27, 28.

Figure 3:
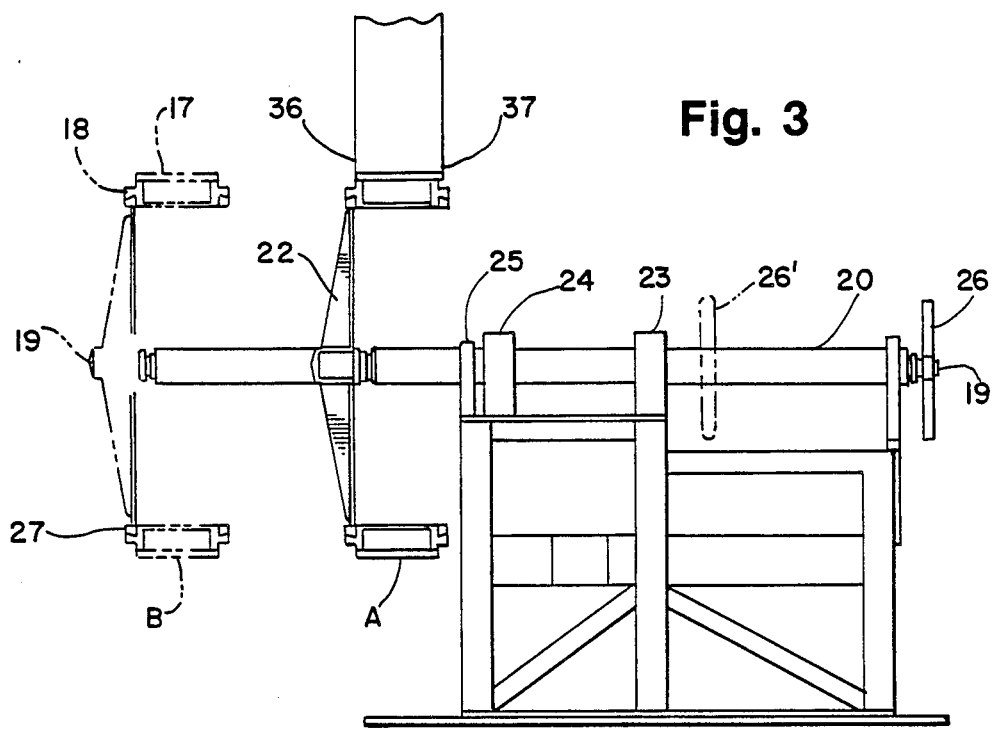
FIG. 3 is a fragmentary, schematic end elevational view showing two positions of the forming drum.

An important feature of the invention is the slidable mounting of the shaft 19 from its drive position A (see FIG. 3) to its conversion position B (see the left hand portion of FIG. 3). This is the condition of the drum 11 featured in FIG. 4 and there it will be seen that the plenum 32 is equipped with rings as at 33 and 34 which develop the sealing engagement of the plenum 32 with the rings 27, 28.

More particularly, the plenum 32 includes a pair of annular plates, the outboard one of which is designated 35 in FIG. 4 and which are advantageously constructed of transparent material such as plexiglass.

Not only is the drum 11 sealed to the plenum 32 during operation, but it is also sealed to the forming hood 12 by virtue of side seals as at 36 and 37—see the upper left hand portion of FIG. 3.

Procedure For Product Change

To achieve a product changeover, viz., develop a diaper having a different pad configuration or size, the outer seal section 36 is removed. The clamp 25 is released and the tube 20, shaft 19 and drum 11 are side-shifted from the position A (see FIG. 3) to the position B. Thereafter, the operator unlatches and removes two adjacent pad forms 18. The operator then installs and latches in one new pad form and thereafter removes the next old pad form. The steps of installing one new pad form and removing the next adjacent old pad form are repeated until all new forms have been installed. The drum 11 is then side-shifted back into running position and the outer seal section or segments are reinstalled.

The invention is particularly advantageous in providing forms constructed to fit an integral number of forms onto the rings 27, 28. For example, a 50" ring seal diameter utilize the following combinations of repeat length and segment numbers:

| Number Segments | Pad or Repeat Length | Drum Circumference | Drum Diameter |
| --- | --- | --- | --- |
| 16 | 12 | 192 | 61.115 |
| 15 | 13 | 195 | 62.070 |
| 14 | 14 | 196 | 62.389 |
| 13 | 15 | 195 | 62.070 |
| 12 | 16 | 192 | 61.115 |
| 12 | 17 | 204 | 64.935 |
| 11 | 18 | 198 | 63.025 |
| 10 | 19 | 190 | 60.479 |
| 10 | 20 | 200 | 63.662 |
| 9 | 21 | 189 | 60.161 |
| 9 | 22 | 198 | 63.025 |
| 9 | 23 | 207 | 65.890 |

While in the foregoing specification a detailed description of an embodiment of the invention has been set down for the purpose of illustration, many variations in the details hereingiven may be made by those skilled in the art without departing from the spirit and scope of the invention.

We claim:

1. A method for facilitating product changeover in the manufacture of fluff pads for disposable diapers wherein fluff from a delivery hood is drawn generally radially inwardly of a rotating drum having a plurality of circumferentially extending screen forms releasably mounted thereon comprising the steps of shifting said drum axially from under said hood and sequentially replacing each screen form of said plurality with another plurality of different sized screen forms.

2. The method of claim 1 in which said hood is equipped with seal means extending radially inwardly of the drum circumference, and removing said seal means from said hood prior to said shifting step.

3. The method of claim 1 in which each screen form is equipped with generally axially aligned clamp means for mounting each screen form on a pair of axially spaced rings on said drum, and opening each clamp means to release the associated screen form.

4. The method of claim 3 in which the one of said rings inward in the direction of said axial shifting is connected to the other of said rings only by way of said screen forms, and maintaining said one ring connected to said other ring during said sequential steps.

5. The method of claim 1 in which said drum rings have a diameter of about 5 feet and said replacing step includes mounting nine to sixteen identical screen forms on said rings, each identical form having an arcuate length in the range of 12" to 23".

6. Apparatus for facilitating product changeover in the manufacture of fluff pads for disposable diapers comprising a frame having a spaced bearing and clamp means, a tube slidably mounted in said bearing and clamp means, a shaft rotatably mounted in said tube and having an end extending beyond said tube, a pad forming drum mounted on said shaft end, said tube being slidable in said bearing means upon release of said clamp means to move said drum from a first position to a second position, a fluff delivery hood on said frame aligned with said drum when the drum is in said first position, said drum in said second position being unaligned with said hood, said drum having a plurality of circumferentially extending screen forms releasably mounted thereon, said forms being releasable from said drum when said drum is in said second position.

7. The apparatus of claim 6 in which said drum includes a pair of axially spaced rings, the ring most outboard of said bearings being equipped with a spider fixedly connecting said outboard ring to said shaft, the inboard of said rings being connected only to said outboard ring, said frame being equipped with a stationary plenum sealed to said rings and equipped with means for applying vacuum to said forms.

8. The apparatus of claim 7 in which said forms are equipped with axially extending, arcuately shaped flanges conforming to the outer contour of said rings, each of said flanges being equipped with latch means for releasably securing said flange to an associated ring.

* * * * *